(12) United States Patent
Ueda et al.

(10) Patent No.: US 7,588,751 B2
(45) Date of Patent: *Sep. 15, 2009

(54) LIPOSOME-CONTAINING RADIOGRAPHIC CONTRAST MEDIUM AND PREPARATION METHOD THEREOF

(75) Inventors: Eiichi Ueda, Akishima (JP); Akihisa Nakajima, Sagamihara (JP); Chiaki Nagaike, Miyakonojo (JP); Yasuyuki Motokui, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 99 days.

This patent is subject to a terminal disclaimer.

(21) Appl. No.: 11/180,849

(22) Filed: Jul. 13, 2005

(65) Prior Publication Data

US 2006/0018828 A1    Jan. 26, 2006

(30) Foreign Application Priority Data

Jul. 21, 2004  (JP) .............................. 2004-213290
Aug. 18, 2004  (JP) .............................. 2004-238505
Aug. 31, 2004  (JP) .............................. 2004-252929
Aug. 31, 2004  (JP) .............................. 2004-252930

(51) Int. Cl.
*A61K 49/00* (2006.01)
*A61K 49/04* (2006.01)

(52) U.S. Cl. ..................... 424/9.1; 424/9.45; 424/9.451

(58) Field of Classification Search ................... 424/9.1
See application file for complete search history.

(56) References Cited

U.S. PATENT DOCUMENTS

| 4,192,859 | A | * | 3/1980 | Mackaness et al. | ......... 424/9.45 |
| 5,326,552 | A | * | 7/1994 | Na et al. | .................. 424/9.455 |
| 5,554,382 | A | * | 9/1996 | Castor | ........................ 424/450 |
| 5,676,928 | A | * | 10/1997 | Klaveness et al. | ......... 424/9.321 |
| 2004/0099976 | A1 | * | 5/2004 | Otake et al. | .................. 264/4.1 |
| 2005/0084453 | A1 | * | 4/2005 | Ueda et al. | .................. 424/9.45 |

FOREIGN PATENT DOCUMENTS

WO        WO 8809165 A1 *  12/1988

OTHER PUBLICATIONS

Sachse et al. (Invest. Radiol. 1997, 32, 44-50; pages provided are numbered 1-8).*
Otake et al. (Langmuir 2001, 17, 3898-3901).*
Shimada et al. (International Journal of Pharmaceutics 2000, 203, 255-263).*

* cited by examiner

*Primary Examiner*—Michael G Hartley
*Assistant Examiner*—Melissa Perreira
(74) *Attorney, Agent, or Firm*—Lucas & Mercanti, LLP

(57) ABSTRACT

A method of pereparing a rediographic contrast medium containing liposomes is disclosed, comprising (a) dissolving a phospholipid and a sterol in a supercritical or subcritical carbon dioxide in the presence of a compound containing a hydroxyl group or a polyalkyleneoxide group, (b) adding thereto an aqueous solution containing an iodine compound to form micelles and (c) discharging the carbon dioxide to form liposomal vesicles enclosing the iodine compound.

17 Claims, No Drawings

US 7,588,751 B2

LIPOSOME-CONTAINING RADIOGRAPHIC CONTRAST MEDIUM AND PREPARATION METHOD THEREOF

This application claims priority from Japanese Patent Application Nos. JP2004-213290 filed on Jul. 21, 2004; JP2004-238505 filed on Aug. 18, 2004; JP2004-252929 filed on Aug. 31, 2004; and JP2004-252930 filed on Aug. 31, 2004 which are incorporated hereinto by reference.

FIELD OF THE INVENTION

The present invention relates to a radiographic contrast medium containing liposome and a preparation method thereof, and in particular to a radiographic contrast medium containing liposome vesicles which are formed by mixing lipid membrane constituents with a supercritical or subcritical carbon dioxide in the presence of at least a compound containing a hydroxyl group or polyalkyleneoxy group and in which nonionic iodine compounds are efficiently and stably enclosed.

BACKGROUND OF THE INVENTION

Investigation or diagnosis using X-rays is the nucleus of current medical image diagnosis. So-called hard tissues such as bones and teeth efficiently absorb X-rays and thereby high contrast X-ray images can be obtained. On the contrary, the difference in X-ray absorption between different soft tissues is relatively small, making it difficult to obtain high contrast images. In such cases, contrast mediums are generally used to obtain high contrast images.

Almost all X-ray contrast mediums which are currently of practical use are contrast medium materials which are water-solubilized compounds containing a triiodophenyl group. The contrast medium is given to a lumen region such as a vascular tract, a ureter or a uterine tube to be used for examination of a form or stenosis of the lumen. However, the foregoing compounds are promptly discharged from the lumen region without interacting with tissue or disease regions, which is not useful for detailed examination of the tissue or disease region, specifically such as cancer tissue. Therefore, an X-ray contrast medium has been desired which can be selectively accumulated in/or onto the targeted tissue or disease region, thereby giving an image which can be distinguished with clear contrast from the circumference or other regions.

A technique of transporting a contrast medium which has been fine-grained and improved in half-life in blood to the targeted tissue is effective to overcome the foregoing problems. There was studied a method in which a contrast medium compound was allowed to be included in a liposome which was comprised of a lipid similar to a biomembrane, and which exhibited low antigenicity. For example, International Publication WO88/09165, ibid WO89/00988, ibid WO90/07491; JP-A No. 07-316079 and 2003-5596 (hereinafter, the term JP-A refers to Japanese Patent Application Publication) propose a liposome containing a non-ionic contrast medium. Further, in the above-mentioned methods, although a liposome exhibiting high safety as raw material and optimal degradability in vivo, organic solvents, specifically chlorinated solvents such as chloroform and dichloromethane were used in the preparation process, as a solvent for phospholipid forming a liposome membrane. Accordingly, the foregoing methods were not practically applicable due to toxicity of retained solvents.

On the other hand, although chemicals soluble in lipid are easily included in a liposome, the included quantity, depending on other factors, is not necessarily large. Although water-soluble electrolytic chemicals can be included in a liposome through interaction of a charge of the chemicals with that of a charged lipid, such a means is not applicable to water-soluble non-electrolytic chemicals. It has been generally desired to allow non-ionic iodine compounds substantially exhibiting low toxicity to be included in a liposome rather than ionic contrast medium compounds, which is not easy from the foregoing reasons. Further, the formed liposome easily formed a multi-layered membrane and the enclosure ratio of the iodine compound was low. Means for allowing a water-soluble non-electrolyte to be efficiently included in a liposome include, for example, a reversed phase evaporation method and an ether injection method. In these means, however, organic solvents are used, producing problems of safety.

JP-A No. 2003-119120 discloses a method of preparing liposome-containing cosmetics or skin medicines for external use by using supercritical carbon dioxide, which is exemplified in the preparation of a skin medicine for external use occluding hydrophilic or hydrophobic medicinal components in a liposome. However, although examples of a water-soluble electrolyte are shown therein as a medicinal component, it is unclear whether a water-soluble non-electrolyte is efficiently included in a liposome using this method. Further, this method is desired to use auxiliary solvents such as ethanol to enhance the enclosure ratio, rendering it difficult to prepare a liposome of a relatively high enclosure ratio without the use of organic solvents. Even if inclusion of a contrast medium material is done well, problems such as its leaking-out over an elapse of time or the situation of the liposome itself becoming unstable must be taken into account. It is further pointed out that since a liposome introduced into an organism is almost always trapped in a reticuloendothelial system such as the liver or spleen, the intended effects cannot be achieved, as described in Cancer Res., 43, 5328 (1983). When iodine compounds are included in a liposome, as is distinct from conventional radiographic contrast medium comprised of an iodine compound in a free form, the form of contrast medium material existing inside and outside of the liposome, the inclusion ratio thereof and the like affect performance of the contrast medium. Accordingly, there is still desired a method of preparing a liposome in which non-ionic iodine compounds are efficiently included and stably maintained, producing no problem in safety.

SUMMARY OF THE INVENTION

There have been extensively made studies to solve the problems as discussed hereinbefore. The present invention has come into being as a result of discovery that retention of contrast medium material using liposome can be improved by the structure of liposome (which are usually formed of lipid bilayer), its stabilization and stabilized enclosure of iodine compounds.

It is therefore an object of the present invention to provide a radiographic contrast medium exhibiting enhanced delivery efficiency and selectivity by enclosing contrast medium material in liposome vesicles.

It is a further object of the invention to provide a radiographic contrast medium containing a liposome and a preparation method thereof in which an iodine compound is enclosed efficiently and stably without use of toxic organic solvents and a preparation method thereof.

The above mentioned objects are realized by method of preparing a radiographic contrast medium comprising a liposome, the method comprising the steps of (a) dissolving a phospholipid and a sterol in a supercritical or subcritical carbon dioxide in the presence of a compound containing a hydroxyl group or a polyalkyleneoxide group, (b) adding thereto an aqueous solution containing an iodine compound to form micelles and (c) discharging the carbon dioxide to form liposomal vesicles enclosing the iodine compound.

The compound containing a hydroxyl group or a polyalkyleneoxide group is preferably a compound containing a polyalkyleneoxide group.

The compound containing a polyalkyleneoxide group is preferably a lipid containing a polyalkyleneoxide group, and more preferably a lipid containing a polyethyleneoxide group.

The above described compound containing a hydroxyl group or a polyalkyleneoxide group is contained preferably in an amount of 0.01 to 1% by weight of the carbon dioxide.

The liposomal vesicles are unilamellar or several-lamellar vesicles.

The iodine compound is contained preferably in an iodine atom amount of 100 to 350 mg I per ml of contrast medium.

The iodine compound is preferably a nonionic iodine compound. Further, the iodine compound is preferably at least one selected from the group of iomeprol, iopamidol, iohexol, iopentol, iopromide, ioxilane, iosimide, iobenzol, iotrolan, iodixanol, iodecimol, iotasl, metrizamide, and 1,3-bis-[N-3, 5-bis-(2,3-dihydroxypropylaminocarbonyl)-2,4,6-tri-iodophenyl]-N-hydroxyacetyl-amio]-propane and more preferably at least one selected from the group of iomeprol, iopamidol, iohexol, iopromide, ioxilane, iotasl, iotrolan and iodixanol.

The liposomal vesicles are dispersed in an aqueous medium, and preferably, 70% to 95% by weight of the iodine compound is not enclosed in the liposome vesicles but exists in the aqueous medium.

The whole lipids contained in the contrast medium is preferably from 20 to 100 mg per ml of the contrast medium.

The weight ratio of the iodine compound enclosed in the liposomal vesicles to the whole lipids is preferably from 3 to 8 (g/g).

The iodine compound is contained preferably at an iodine atom amount of 200 to 300 (more preferably 240 to 300) mg I per ml of contrast medium, in combination with whole lipids contained in the contrast medium at 20 to 80 mg/ml.

The molar ratio of [phospholipid (which does not include PEG-phospholipid)]/(sterol) is preferably from 100/60 to 100/90.

The molar ratio of [phospholipid (which does not include PEG-phospholipid)]/(lipid containing a polyalkyleneoxide group) is preferably from 100/5 to 100/10.

The above described liposome vesicles preferably have an average size of 0.05 to 0.8 μm.

The aqueous solution containing an iodine compound preferably contains at least one selected from the group consisting of a water-soluble amine buffer, edetate calcium disodium (or EDTA $Na_2$—Ca), an inorganic salt, an osmotic pressure-adjusting agent and a preservative.

The aqueous phases existing inside and outside the liposome vesicles each contain preferably cations as chloride salts, phosphate salts or hydrogen carbonate salts and satisfying the following requirement:

$$[Na^+]+126 \cdot [Ca^{2+}]+50 \cdot [K^+] \leq 130$$

wherein $[Na^+]$ is a sodium ion content of 20 to 70 mM, $[Ca^+]$ is a calcium ion content of 0.1 to 0.6 mM and $[K^+]$ is a potassium ion content of 0.4 to 0.8 mM; and a magnesium ion content is 0.5 to 0.8 mM.

DETAILED DESCRIPTION OF THE INVENTION

The present invention is directed to a method of preparing a radiographic contrast medium including liposome vesicles enclosing an aqueous phase inside the lipid membrane which contains an iodine compound; the liposome is prepared by mixing lipid membrane constituents forming lipid membrane with supercritical or subcritical carbon dioxide, in the presence with a compound containing a hydroxyl group or a polyalkyleneoxide group and the liposome substantially does not contain any chlorinated solvent or other organic solvents.

Radiographic Contrast Medium

Liposome is usually a structure formed of a lipid membrane, i.e., a lipid double layer. The radiographic contrast medium of the invention is one which is comprised of a liposome containing substantially no chlorinated solvent, in which iodine compounds as contrast medium material are included in the aqueous phase in the interior of a lipid membrane. In one preferred embodiment thereof, the contrast medium contains an iodine compound and at least one auxiliary additive (pharmaceutical preparation aid) in the water phase inside the liposome membrane and in an aqueous medium in which the liposome vesicles are dispersed, in which the respective concentrations preferably are substantially the same between inside and outside the membrane. The expression, substantially the same means concentrations being nearly the same. In the specification, liposome membrane is also referred to as lipid membrane.

An auxiliary additive refers to a compound which is to be added together with the contrast medium material and various substances can be employed based on techniques for preparing contrast mediums. Specific examples thereof include physiologically acceptable buffering agents, edetate chelating agents such as EDTA $Na_2$—Ca (or disodium calcium ethylenediaminetetraacetate) or EDTA $Na_2$ (or disodium ethylenediaminetetraacetate) and optionally, an osmotic pressure-adjusting agent, a stabilizer, an antioxidant such as α-tocopherol, and a viscosity adjusting agent. Water-soluble amine type buffering agents and chelating agents are preferably included. As a pH buffering agent, amine-type buffering agents and carbonate type buffering agents are preferred, of which amine type buffering agents are more preferred and trometamol (also denoted as tromethamine or 2-amino-2-hydroxymethyl-1,3-propanediol) is specifically desirable. Of chelating agents preferable is $EDTANa_2$—Ca (edetate calcium disodium).

An aqueous medium refers to a solvent which is basically composed of water capable of dissolving iodide compounds or auxiliary additives. There is usable sterilized water containing no exothermic material. An aqueous solution, other than the water phase inside the liposome membrane (or an included aqueous solution), namely, an aqueous medium in which the liposome vesicles are dispersed, also contains the iodine compound and auxiliary additive(s), such as a water-soluble amine type buffering agent or chelating agents. Accordingly, no difference in osmotic pressure is caused between inside and outside of the membrane, whereby structure stability of the liposome is maintained.

Contrast Medium Compound

Iodine compounds usable as contrast medium material are preferably water-soluble iodine compounds. Any ionic or nonionic water-soluble iodine compound capable of functioning as a contrast medium is usable in the inventions. Nonionic iodine compounds, which generally exhibit a lower osmotic pressure than ionic iodine compounds, are preferred. Specifically, water-soluble nonionic iodine compounds containing at least one iodophenyl group such as a 2,4,6-triiodophenyl group (e.g., nonionic triiodobenzoic acid type) are preferred in this invention. Such iodine compounds are contained preferably in an iodine atom amount of from 100 to 350 mg I/ml.contrast medium.

Preferred examples of such a nonionic iodine compound include iomeprol, iopamidol, iohexol, iopentol, iopromide, ioxilane, iosimide, iobenzol, iotrolan, iodixanol, iodecimol, iotasl, metrizamide, and 1,3-bis-[N-3,5-bis-(2,3-dihydroxypropylaminocarbonyl)-2,4,6-triiodophenyl]-N-hydroxyacetyl-amio]-propane. Of these, iomeprol, iopamidol, iohexol, iopromide, ioxilane, iotasl, iotrolan and iodixanol are more preferred.

Further, examples of the nonionic iodine compounds include diatrizoic acid, diatrizoate sodium, meglumine diatrizoate, acetorizoic acid and its soluble salt, diprotrizo acid, iodamide, iodipamide sodium, meglumine iodipamide, iodohippuric acid and its soluble salt, iodomethamic acid, iodopyracet, iodo-2-pyrridone-N-acetic acid, 3,5-diiodo-4-pyridone-N-acetic acid (iodopyracet), diethylammonium salts of the foregoing acids, iothalamic acid, metrizoic acid and its salt, iopanoic acid, iocetamic acid, iophenoic acid and its soluble salt, sodium thyropanoate, sodium iopodate and other similar iodinated compounds.

It is preferred that 70% to 95% by weight of total iodine compounds contained in the contrast medium is not included in the interior of the liposome vesicles but exists in the aqueous medium in which the vesicles are dispersed.

The weight ratio of the iodine compound enclosed in the liposome vesicles to the foregoing total lipid amount is preferably from 3 to 8 (g/g). The liposome vesicles are each preferably a unilamellar vesicle or a several-lamellar vesicle (that is a vesicle formed of several lipid membranes).

The total lipid content of the contrast medium of the invention is preferably from 20 to 100 mg/ml, more preferably from 20 to 80 mg/ml, still more preferably from 40 to 90 mg/ml, and most preferably from 50 to 80 mg/ml. In that case, the total lipid means whole lipids forming the liposome, including phospholipids, sterols and glycols.

These iodine compounds may be used alone or in combination. The iodine compounds usable in this invention are not limited to the foregoing exemplified compounds and include not only a free form but also its salt and hydrate.

As iodine compounds suitable for radiographic contrast medium of this invention are preferred iomeprol, iopamidol, iotrolan and iodixanol, which exhibit high hydrophilicity and a low osmotic pressure even at relatively high concentration. Specifically, dimeric nonionic iodine compounds such as iotrolan and iodixanol have advantages such that when prepared in the same iodine concentration, the prepared contrast medium has a lower overall molar quantity, resulting in a reduced osmotic pressure.

The concentration of the water-soluble iodine compound contained in the contrast medium according to this invention can be arbitrarily set based on factors such as properties of the contrast medium compound, the intended dosage route of a medicine and clinical guidelines. The quantity of the water-soluble iodine compound included in a liposome is typically 5% to 95% by weight, preferably 5 to 90% and more preferably 5 to 70% by weight, based on total iodine compounds contained in the contrast medium. Specifically, to prevent unstabilization of the liposome including a capsulated iodine compound of the invention, the water-soluble iodine compound included in the liposome is usually from 5% to 35%, preferably from 5% to 30%, and more preferably from 5% to 25% by weight, based on the total iodine compound. If the proportion of a water-soluble iodine compound included within liposome vesicles accounts for 5% to 30% by weight (preferably 5% to 25% by weight) of the total iodine compound contained in the contrast medium, effluent of the included iodine compound to the aqueous dispersion outside the vesicles, in which the residual 70% to 95% by weight (or 75% to 95% by weight) exists, can be substantially ignored. Accordingly, encapsulation of the iodine compound can prevent unstabilization due to the osmotic pressure effect of the liposome, leading to enhanced stability of contrast medium material.

In light of the foregoing, the weight of iodine atoms included in the water phase inside the liposome membrane of the contrast medium is from 10 to 200 mg/ml, preferably from 20 to 180 mg/ml, and more preferably from 70 to 110 mg/ml. This is a parameter which is also defined by the foregoing enclosure ratio and the total iodine content.

Liposome

In the radiographic contrast medium of the invention, the foregoing contrast medium compounds are used in the form of enclosure in a liposome as a micro-carrier to efficiently and selectively deliver the contrast medium compounds to the targeted region such as a targeted organ or tissue. The contrast medium can enhance its retention in the blood using a liposome with improved blood stability, thereby achieving efficient pharmaceutical delivery and targeting. An improvement of closely related holding efficiencies such as the stabilized liposome structure and retention stability of included material and characteristics such as blood stability and blood retentivity are required to produce EPR (Enhanced Permeability and Retention) effect which is effective to achieve superior representation of tumors.

In the radiographic contrast medium of this invention, appropriate design of the vesicle size and bimolecular membrane of the liposome including a contrast medium compound can achieve targeting functions, in which both passive targeting and active targeting are taken into account. The former can control biological behavior through adjustment of vesicle size, lipid composition or charge of the liposome. Adjustment of the liposome vesicle size to a narrow range can be easily accomplished by the method to be described later. Design of the liposome membrane surface can be achieved by varying the kind and composition of phospholipids and included material to provide desired characteristics.

There should be also examined the introduction of active targeting which enables higher integrality and selectivity of the contrast medium. For example, introduction of a polymer chain of polyalkylene oxide or polyethylene glycol (PEG), which can control the guidance process to the targeted region, is extremely beneficial. A liposome suitable for the contrast medium of the invention is one in which the surface is modified with polyalkylene oxide or PEG to enhance blood retention and one which is not easily binged by reticuloendothelial cells such as liver. The contrast medium which does not reach cancerous tissue or the diseased region is externally discharged without being accumulated in the normal region, before causing adverse effects by the degradation of the liposome. This can be attained by optimal control of stability of a liposome in relation to the external discharge time in the design of the liposome. Iodine compounds as contrast medium material can be promptly discharged into urine via the kidney, thereby preventing adverse influences caused by internal retention in vain and delaying adverse effects.

In general, a phospholipid and/or a glycolipid are preferably used as a constituent of a lipid membrane (or lipid bilayer) of the liposome. In the invention, the liposome contained in the radiographic contrast medium is prepared by mixing constituents forming the lipid membrane and supercritical or subcritical carbon dioxide in the presence of at least a compound containing a hydroxyl group or a compound containing a polyalkyleneoxide group, as described later.

Examples of a preferred neutral phospholipid in the liposome include lecithin and lysolecithin obtained from soybean or egg yolk, and their hydrogenation products or hydroxide derivatives. Further, examples of phospholipids include phosphatidylcholine, phosphatidylserine, phosphatidylinositol, phosphatidylglycerol, phosphatidylethanolamine, and sphingomyelin, which are derived from egg yolk, soybeans or other plants and animals, or are semi-synthetically obtainable; phosphatidic acid, dipalmitoylphosphatidylcholine (DPPC), distearoyl-phosphatidylcholine (DSPC), dimyristoylphosphatidylcholine (DMPC), dioleylphosphatidylcholine (DOPC), dipalmitoylphosphatidylglycerol (DPPG), distearoylphosphatidylserine (DSPS), distearoylphosphatidylglycerol (DSPG), dipalmotoylphosphatidylinositol (DPPI), distearoylphosphatidylinositol (DSPI), dipalmitoylphosphatidic acid (DPPA) and distearoylphosphatidic acid (DSPA), which are synthetically obtainable.

Examples of cationic lipids usable in the invention include 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxy)propyl]-N,N,N-trimethylammonium chloride (DOTMA), 2,3-dioleyloxy-N-[2(spermine-carboxamido) ethyl]-N,N-dimethyl-1-propaneaminiumtrifluoroacetate (DOSPA) and N-[1-(2,3-dimyristyloxy)propyl]-N,N-dimethyl-N-(2-hydroxyethyl)ammonium bromide (DMRIE).

Examples of a cationic phospholipid include an ester of phosphatidic acid and an aminoalcohol, for example, ester of dipalmitoylphosphatidic acid (DPPA) or distearoylphosphatidic acid (DSPA) and hydroxyethylenediamine. These cationic lipids are contained in an amount of 0.1% to 5% by weight, preferably 0.3% to 3% by weight, and more preferably 0.5% to 2% by weight of the total lipid amount.

These phospholipids may be used alone or in two or more combinations. Two or more charged phospholipids are preferably used in combination of negative-charged phospholipids or in combination of positive-charged phospholipids in term of prevention of aggregation of the liposome. The combined use of a neutral phospholipid and charged phospholipid is preferably in a weight ratio of 200:1 to 3:1, more preferably 100:1 to 4:1, and still more preferably 40:1 to 5:1.

Examples of glyceroglycolipids include glycerolipids such as digalactosyldiglyceride and digalactosyldiglyceride sulfuric acid ester; sphingoglycolipids such as galactosylceramide, galactosylceramide sulfuric acid ester, lactosylceramide, ganglioside G7, ganglioside G6 and ganglioside G4.

In addition to the foregoing lipids, other substances may optionally be incorporated as a constituent of the liposome membrane. For example, cholesterol, dihydrocholesterol, cholesterol ester, phytosterol, sitosterol, stigmasterol, campesterol, cholestanol, lanosterol and 2,4-dihydroxylanosterol are cited as a layer stabilizer. Further, sterol derivatives such as 1-O-sterolglucoside, 1-O-sterolmaltoside and 1-O-sterolgalactoside have been shown to be effective in stabilization of liposome (as described in JP-A No. 5-245357) and of the foregoing sterols, cholesterol is specifically preferred. Sterols are used usually in an amount of from 0.05 to 1.5 parts by weight, preferably from 0.2 to 1 parts by weight and more preferably from 0.3 to 0.8 parts by weight per part by weight of phospholipid. An amount of less than 0.05 parts by weight does not achieve stabilization by a sterol to enhance dispersibility of mixed lipids, and an amount of more than 2 parts by weight inhibits liposome formation or results in unstable formation thereof.

A cholesterol enclosed in the liposome membrane is capable of functioning as an anchor to introduce a polyalkylene oxide. Concretely, cholesterol which is included in the membrane as a liposome membrane constituent may optionally be linked via an anchor to a polyalkylene oxide group. A short chain alkylene group or oxyalkylene group can be used as an anchor. JP-A No. 9-3093 discloses novel cholesterol derivatives, in which various functional substances can be efficiently fixed at the top of a polyoxyalkylene chain, which can be employed as a liposome constituent.

Sterols are used preferably in a molar ratio of phospholipid (not including PEG-phospholipid)/sterols of 100/60 to 100/90 and more preferably 100/70 to 100/85. The molar ratio is based on the amount of phospholipid which does not include PEG-phospholipid. A molar ratio of less than 100/60 cannot achieve stabilization of dispersion of the lipid mixture.

In addition to the foregoing sterols, glycols may be added as a constituent of a liposome vesicular membrane. In the preparation of liposome, addition of a phospholipid together with glycols enhances the holding efficiency of a water-soluble iodine compound included within liposome vesicles. Examples of glycols include ethylene glycol, diethylene glycol, triethylene glycol, propylene glycol, dipropylene glycol, trimethylene glycol, 1,4-butanediol, 1,5-pentanediol, neopentyl glycol, 1,6-hexanediol, 1,7-heptanediol, 1,8-octanediol, 1,9-nonanediol, 1,10-decanediol and pinacol. Glycols are used preferably in an amount of 0.01% to 20% by weight of the total weight of lipids, and more preferably 0.5% to 10% by weight.

Other additive compounds include, for example, as a negative charge-providing material, phosphoric acid alkyl esters such as diacetyl phosphate and as positive charge-providing material, aliphatic amines such as stearylamine.

Using a compound containing a hydroxyl group or a polyalkyleneoxide (PAO) group (preferably, a phospholipid or cholesterol containing a polyalkyleneoxide group or the like), preparation of a liposome with carbon dioxide in the supercritical or subcritical state results in a liposome exhibiting a relatively high enclosure ratio, without using any organic solvent. To overcome problems such as being trapped in a reticuloendothelial cell and problems regarding instability of liposome itself such as destruction or aggregation, there was attempted introduction of a polymeric chain, such as polyethylene glycol (PEG) chain (or polyoxyethylene group, $-(CH_2CH_2O)_n-H$) onto the liposome surface, as described in JP-A No. 1-249717 and FEBS letters 268, 235 (1990).

Attachment of a polyalkylene oxide chain (or polyoxyalkylene chain) or a PEG chain onto the liposome vesicular surface can provide a new function to the liposome. For example, such a PEG-modified liposome can be expected to have an effect of becoming less recognizable from an immune system (so-called state of being stealthy). It was proved that a liposome having a hydrophilic tendency increased blood stability and thereby the concentration in blood can be stably maintained over a long period of time, as described in Biochim. Biophys. Acta., 1066, 29-36 (1991). JP-A No. 2002-37833 disclosed a technique in which a phospholipid modified with a polyalkylene oxide was incorporated into the liposome membrane to enhance blood retentivity of the liposome. Such a liposome was also shown to exhibit improved aging stability.

Employment of the foregoing properties can provide organ-specificity to the radiographic contrast medium of the invention. For example, since lipid components are easily accumulated in liver, the use of a liposome containing no PEG or trace amounts of PEG is desired to selectively provide contrast to the liver. Increasing the vesicle size to 200 nm or more results in increased possibility of being promptly incorporated by phagocytosis of liver Kupffer cells, leading to accumulation in the said site of the liver. In imaging liver cancer, since cancerous tissue has fewer Kupffer cells than normal tissue, incorporation of the contrast medium liposome becomes a less amount, forming clear contrast.

In the case of imaging other organs, the liposome becomes a state of being stealthy by introduction of a PEG, becoming difficult to be gathered in the liver, therefore, the use of a PEG-modified liposome is recommended. Introduction of a PEG forms a hydration sphere, thereby stabilizing the liposome and enhancing blood retention. Functions can be adjusted by changing a length of oxyethylene units of a PEG and its introducing ratio. Polyethylene glycol having 10 to 3500 (preferably, 100 to 2000) oxyethylene units is preferred as PEG. A PEG is preferably contained in an amount of 1% to 40% by weight, and more preferably 5% to 25% by weight, based on the lipid constituting the liposome.

PEG-modification of a liposome can be accomplished using commonly known techniques. For example, a polyethylene glycol (PEG) group linked to an anchor compound (e.g., cholesterol) is mixed with a phospholipid as a membrane constituent to form a liposome and the anchor compound may be allowed to be linked to an activated PEG group. Since the PEG group introduced onto the liposome surface is unreactive with "functional material" to be described later, it is difficult to fix the functional material onto the liposome surface. Instead thereof, PEG, the top of which has been chemically modified is bonded to a phospholipid, which is included as a constituent for liposome to prepare liposome.

In place of polyethylene glycol (PEG), commonly known polyalkylene oxide groups may be introduced, which is represented by general formula: $-(AO)_n-Y$, wherein AO is an oxyalkylene group having 2 to 4 carbon atoms, n represents a mean addition molar number and is a positive number of 1 to 2000 (preferably, 10 to 500, and more preferably 20 to 200); and Y is a hydrogen atom, an alkyl group or a functional group. Examples of an oxyalkylene group having 2 to 4 carbon atoms include an oxyethylene group, oxypropylene group, oxytrimethylene group, oxytetramethylene group, oxy-1-ethylethylene group and oxy-1,2-dimethylethylene group.

When n is 2 or more, plural oxyalkylene groups may be the same or differ. In the latter case, differing oxyalkylene groups may be in a random form or in a block form. To provide hydrophilicity to an oxyalkylene group, ethylene oxide alone is preferably addition-polymerized, in which n is preferably 10 or more. In cases when different alkylene oxides are addition-polymerized, it is desirable that at least 20 mol % (preferably at least 50 mol %) of ethylene oxide is addition-polymerized. To provide lipophilicity to an oxyalkylene group, it is preferred to increase the molarity of alkylene oxide(s) other than ethylene oxide. For example, a liposome containing a block copolymer of polyethylene oxide and polypropylene oxide (or polyethylene oxide-block-polypropylene oxide) is one preferred embodiment of this invention.

The functional group of the foregoing Y is to attach functional material such as sugar, glycoprotein, antibody, lectin and a cell adhesion factor to the top of a polyalkylene oxide group and examples thereof include an amino group, oxycarbonylimidazole group and N-hydroxysuccinimide. The liposome anchoring a polyalkylene oxide chain, to the top of which the foregoing functional material is bonded, not only exhibits effects due to introduction of a polyalkylene oxide group but also gives full play of functions of the functional material, for example, a function as a recognition element, such as directivity to a specific organ (namely organotropism) and cancer tissue directivity.

A phospholipid or cholesterol which contains a polyalkylene oxide group can be used alone or in combinations thereof. The content thereof preferably is 0.001 to 50 mol %, more preferably 0.01 to 25 mol %, and still more preferably 0.1 to 10 mol %, based on the total amount of liposome membrane forming components. A content of less than 0.001 mol % results in reduced expected effects.

With respect to phospholipid polyalkylene oxide derivatives were proposed modified phospholipids represented by the following formula, as described in JP-A No. 7-165770:

formula

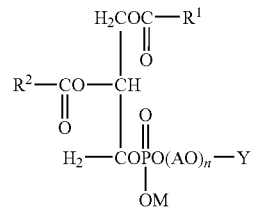

wherein $R_1$ and $R_2$ are each an alkyl group having 2 to 29 carbon atoms; M is a hydrogen atom or an alkali metal atom such as sodium or potassium; AO n and Y are each the same as defined in the foregoing.

Specific examples thereof include polyethylene oxide (PEO) derivatives of a phosphatidylamine and the like, such as distearoylphosphatidyldiethanolamine polyethyleneoxide (DSPE-PEO). Further, JP-A No. 2002-37883 discloses extremely purified, polyalkylene oxide-modified phospholipid to prepare a water-soluble polymer-modified liposome exhibiting enhanced blood retentivity. It is also disclosed that the use of a polyalkylene oxide-modified phospholipid having a relatively low monoacyl content in the preparation of liposome leads to superior aging stability of liposome dispersions.

Preparation of Liposome

The preparation method of a radiographic contrast medium according to the invention is characterized in that, in the presence of a compound containing a hydroxyl group or a polyalkyleneoxide group, a phospholipid as a lipid membrane constituent and at least one of cationic lipids and sterols are mixed with supercritical or subcritical carbon dioxide, then an aqueous solution of an iodine compound is introduced thereto to form micelles (bimolecular layer micells) and thereafter, the carbon dioxide is discharged to form liposomal vesicles enclosing an aqueous core containing the iodidine compound. The aqueous iodine compound solution preferably further contains auxiliary additives.

There have been proposed various methods for preparing liposomes. Different methods often finally lead to liposomes extremely differing in form and characteristics, as described in JP-A No. 6-80560. Therefore, a method is optimally chosen in accordance with the form or characteristics of a desired liposome. In general, a liposome is prepared by dissolving lipid components such as phospholipid, sterol and lecithin, almost without an exception, in organic solvents such as chloroform, dichloromethane, ethyl ether, carbon tetrachloride, ethyl acetate, dioxane or tetrahydrofuran (THF). Specifically, chlorinated solvents are often employed. The thus prepared liposome necessarily contains an organic solvent. Accordingly, a treatment of a multi-step process over a long time is required to remove residuak organic solvents. It is difficult to completely remove residual organic solvents, specifically, chlorinated organic solvents, which is of concern for adverse effects on organisms.

To prepare liposome used in this invention, a preparation method using supercritical or subcritical carbon dioxide is employed to avoid the foregoing problems. Carbon dioxide is suitable because it exhibits a critical temperature of 31.1° C. and a critical pressure of 75.3 kg/cm$^2$ and can be relatively easily handled, is an inert gas and non-toxic to the human body even when being remained, and a high-purity liquid is inexpensively and easily available. The liposome prepared by this method has preferred characteristics and advantages to include iodine compounds used as a radiographic contrast medium, as described later.

The preparation of liposome using supercritical or subcritical carbon dioxide needs to dissolve or disperse constituents of the lipid membrane in carbon dioxide in the supercritical state (including the subcritical state). Dissolution, dispersion or mixing is conducted preferably in the presence of a compound containing a hydroxyl group, as a solubilizing agent (or auxiliary solvent).

Compound containing a hydroxyl group (or hydroxyl group-containing compounds) described above include compounds which contain a hydroxy group, a polyol group, a polyalkyleneglycol ether group, or a combination of polyol/polyglycol ether group, as a hydrophilic group. The hydroxyl group containing compound usable as a solubilizing agent is preferably one which exhibits affinity with lipid membrane constituents such as a phospholipid or cholesterol and easily miscible with it. Amphiphilic one which exhibits optimal hydrophilicity and lipophilicity is suitable to disperse lipid membrane constituents in polar carbon dioxide fluid (or liquid).

Saccharides are also usable as a hydroxyl group-containing compound. Specifically, monosaccharides include, for example, hexoses such as dehydroascorbic acid, pentaerythritol, sorbitol, glucose, fructose, galactose, mannose, glucosamine, galactosamine, mannosamine and N-acetyglucosamine, and pentoses such as xylose, ribose and arabinose. Oligosaccharides include, for example, disaccharides such as maltose, lactose, trehalose and isomaltose, maltotriose, isomaltotriose, mannotriose, manninotriose, maltotetraose, and maltopentaose. Further polysaccharides include, for example, cellulose and amylose (or starch) but are not limited to these.

When there is an apprehension of toxicity of a residual solubilizing agent, it is desirable not to use lower alcohols as the hydroxyl group-containing compound in terms of safety. Taking into account effectiveness and safety, the solubilizing agent is preferably a compound containing a polyethylene glycol group, and more preferably a lipid containing a polyethylene glycol group, in which the polyethylene glycol group having an oxyethylene unit of 10 to 3500 (preferably 100 to 2000) is preferred.

The use of one or more hydroxyl group-containing compounds enhances the enclosure ratio. Hydroxyl group-containing compounds are used as a solubilizing agent, preferably in an amount of 0.01% to 1% by weight of supercritical or subcritical carbon dioxide and more preferably 0.1% to 0.8% by weight.

The temperature of a supercritical or subcritical carbon dioxide used in the invention is usually from 25° to 200° C., preferably from 31° to 100° C., and more preferably from 35° to 80° C. The pressure thereof is usually from 50 to 500 kg/cm$^2$, preferably from 100 to 400 kg/cm$^2$, and the pressure of 90 to 150 kg/cm$^2$ is specifically preferred.

The preparation of a liposome used for the radiographic contrast medium of the invention is conducted in the following manner. Liquid carbon dioxide is added to a pressure vessel and brought to the supercritical state or subcritical state under the suitable pressure and temperature described above. Into the supercritical (or subcritical), a phospholipid as a lipid membrane constituent of liposome and a material to stabilize the lipid membrane are dissolved or dispersed in the presence of the foregoing hydroxyl group-containing compound. There may be added a cationic phospholipid or polyalkylene oxide-containing compound (for example, a polyalkylene oxide-modified phospholipid) as a membrane lipid. Alternatively, liquid carbon dioxide may be added into a pressure vessel in which the foregoing compounds are added in advance and brought to the supercritical state by adjusting the temperature and pressure. Subsequently, an aqueous solution containing an iodine compound and optionally, auxiliary additives, as described earlier are introduced to the formed supercritical carbon dioxide containing a phospholipid and a material to stabilize the lipid membrane to form micelles. There may be reversed the adding side and the added side. After completion of mixing, the inside of the vessel is evacuated to discharge carbon dioxide to form an aqueous dispersion in which the iodine compound is enclosed in the interior of the liposome. In this case, the iodine compound may be contained in a water phase (external water phase) outside the vesicles besides the water phase in the interior of the liposome vesicles. Since the foregoing aqueous solution is included in the interior of the liposome vesicles, the iodine compound is present not only in the external water phase but also mainly in the water phase in the interior of the liposome vesicles, which is in the state of so-called enclosure. Further, the liposome is allowed to pass through a porous filter having a pore size of 0.1 to 1.0 μm (preferably 0.1 to 0.5 μm). Subsequently, via the pharmaceutical preparation process such as a sterilization treatment and packaging, the radiographic contrast medium of the invention is prepared.

The preparation of liposome using supercritical or subcritical carbon dioxide has been proved to be high in liposome formation rate, inclusion percentage of including material and remaining ratio of included material in liposome, as described in JP-A No. 2003-119120. Further, the foregoing method of this invention, which is applicable even on an industrial scale and enables effective inclusion of a nonionic water-soluble material in a liposome, substantially without using any organic solvent, is useful for preparation of the radiographic contrast medium of this invention. The foregoing expression, substantially without using any organic solvent means that the residual organic solvent content is not more than 10 µg/l.

Preparation of Radiographic Contrast Medium

The liposome used for the radiographic contrast medium of the invention is desirably one which is comprised substantially of a single membrane or a few membranes. The liposome of a single membrane is a liposome which is comprised of unilamellar vesicles, that is, a unilamellar vesicle formed of a single phospholipid bilayer. The liposome comprised substantially of a single membrane means that vesicles are each made up of a phospholipid bilayer, the replica of which is recognized nearly as a single layer in transmission electron microscopic observation using a freeze fracture replica technique. Thus, when observing the imprint of particles remaining in the carbon film, one having no difference in level is judged as a unilamellar vesicle and one having two or more differences is a multilamellar vesicle. The foregoing expression, substantially means that such unilamellar vesicles are contained preferably in an amount of at least 80%, and more preferably at least 90%, based on the total liposome amount, i.e., the total amount of vesicles contained in the radiographic contrast medium.

The single membrane liposome or liposome comprised of a few membranes, that is, unilamellar vesicles can be efficiently prepared using the foregoing supercritical carbon dioxide as a solvent for lipids and by a phase separation method using water. On the contrary, in conventional methods for preparation of liposome, a liposome comprised of multilamellar vesicles (MLV), that is, multilamellar vesicles often account for a fairly high proportion. Accordingly, operations such as exposure to ultrasonic or filtering through given-sized pores are required to raise the proportion of unilamellar liposome. Unilamellar vesicles have advantages such that an amount of added liposome or a given lipid amount is usually less than that of multilamellar vesicles.

A unilamellar vesicle, specifically, a large unilamellar vesicle (LUV) advantageously has a larger inclusion capacity than a multilamellar vesicle. A liposome used in the radiographic contrast medium is between LUV having a size of 0.2 to 1 µm and small unilamellar vesicles (SUV) of less than 0.05 µm. Accordingly, the retention volume exceeds the SUV and the trapping efficiency of a water-soluble iodine compound, in other words, the inclusion efficiency thereof becomes superior, as described later. Further, differing from MLV or LUV, this vesicular liposome does not rapidly disappear from the bloodstream due to incorporation into reticuloendothelial cells. However, even unilamellar vesicles exhibiting superior inclusion efficiency of an iodine compound lower their stability when the weight of an included iodine compound is relatively excessive. Specifically, there was observed a tendency of being weak for rapid change of ionic strength. The liposome used in the contrast medium of the invention was adjusted to a relatively small vesicle size and incorporation of at least a compound selected from compounds containing a polyalkyleneoxide group (for example, phospholipid), sterols and glycols into the vesicle membrane led to enhanced stability of the lipid membrane. As a result, it was proved that such liposome was resistant to salt shock.

The vesicular particle size (or liposome vesicle size, hereinafter, also denoted simply as vesicle size) of the liposome, as microparticles and its distribution are closely correlated with enhanced blood retention property, targeting ability and delivery efficiency which are aimed in the invention. The vesicle size can be determined in such a manner that a dispersion containing liposome vesicles enclosing an iodine compound is frozen and fractured, following which carbon is vapor-deposited onto the fractured interfaces and the deposited carbon is observed with an electron microscope (freeze fracture TEM method). The vesicle size can be adjusted by formulation or control of processing conditions. For example, increasing the supercritical pressure described earlier results in a liposome of a reduced vesicle size. Filtration may be conducted using a polycarbonate film to allow the vesicle size distribution to fall within a narrower range. In this regard, a liposome of unilamellar vesicles at an average vesicle size of not more than 0.4 µm can be efficiently obtained by passing it through an extruder incorporating a filter of 0.1 to 0.5 µm pore size. In this invention, the average particle size refers to a simple (or arithmetic) average of the given number of observed vesicular particles of the contrast medium, for example, 20 vesicles. This value usually agrees with or is close to the central vesicle size which refers to a vesicle size having the highest frequencies in the vesicle size distribution. Introduction of such an extrusion operation, in addition to the foregoing sizing operation, has advantages such as adjustment of the concentration of the iodine compound existing outside the liposome vesicles, change of liposome dispersing solution and removal of unintended material.

Sizing of the liposome particles is important to enhance active targeting capability of the liposome. For example, Japanese Patent No. 2619037 discloses that unfavorable retention in lung capillaries can be avoided by removal of liposome of 3 µm or more. However, liposome of 0.5 to 3 µm does not necessarily exhibit tumor directivity.

The average vesicle size of a liposome used in the contrast medium of the invention preferably is 0.05 to 0.5 µm, more preferably 0.05 to 0.2 µm, and still more preferably 0.05 to 0.13 µm. The vesicle size can be adjusted in accordance with the objective of X-ray imaging. For example, when 0.11 to 0.13 µm is preferred for the purpose of selective imaging of a tumor region. Adjusting the liposome vesicle size so as to fall within the range of 0.1 to 0.2 µm (preferably 0.11 to 0.13 µm) enables selective concentration of the contrast medium to cancerous tissue. This is known as the EPR effect. The pore on the vascularized wall of solid cancerous tissue is abnormally larger than a 30 to 80 nm pore size of the capillary wall fenestra of normal tissue, so that even a large molecule of ca. 0.1 to ca. 0.2 µm leaks through the vascular wall. Thus, the EPR effect is due to permeability of the vascularized wall of cancerous tissue which is higher than the microvascular wall of normal tissue.

Since lymphatic vessels do not sufficiently develop around cancerous tissue, the contrast medium leaking through vascular walls does not return to the blood vessel and remains there for a relative long time. The EPR effect is a passive conveyance employing the bloodstream so that enhanced blood retention is required to effectively develop the effect. Thus, contrast medium particles (or liposome vesicular particles including an iodine compound) are required to be retained in blood and to pass many times through blood vessels near cancer cells. The radiographic contrast medium of this invention, which does not contain any particularly large particle, does not easily become a target for trapping by reticuloendothelial cells. Liposome vesicles, which are in a form similar to an erythrocyte and also behaves similarly to an erythrocyte, are long retained in blood and not promptly discharged via the kidneys and further not binged by reticuloendothelial cells when being masked. The EPR effect necessarily enhances transfer of the contrast medium compound to the targeted organ or tissue and achieves selective concentration and accumulation in cancerous tissue of the contrast medium. A rise of the accumulation ratio of oncocyte/normal cell enhances contrast performance of the contrast medium. Improved tumor visualization enables finding-out a micrometastatic cancer which has up to now been difficult to detect.

In cases when an iodine compound is enclosed in the liposome as a microcarrier, in addition to the delivery efficiency and retention stability of the contrast medium material, the amount of lipid membrane must be taken into account. An increase of the lipid amount increases the viscosity of the contrast medium. The amount of an iodine compound enclosed in the liposome vesicles, which is contained in an aqueous solution included in liposome vesicles, is preferably from 1 to 10, more preferably from 3 to 8, and still more preferably from 5 to 8, in terms of the weight ratio of the iodine compound included in the vesicles to the lipid forming the vesicular membrane.

A weight ratio of the iodine compound enclosed in the liposome vesicles of less than 1 necessitates injection of a relatively large amount of the lipid, resulting in lowered delivery efficiency of the contrast medium material. According to Japanese Patent No. 2619037, even a weight ratio of 1 was described to be a relatively high value in light of the technical level at that time. Since the viscosity of the radiographic contrast medium depends on the lipid content of the liposome, liposome formed of a single membrane (unilamellar vesicles) or liposome formed of several membranes which exhibits enhanced retention volume and enclosure efficiency is apparently advantageous. On the contrary, when the weight ratio of the included iodine compound to the lipid of the liposome membrane exceeds 10, the liposome becomes structurally unstable and diffusion or leakage of the iodine compound from the liposome membrane is unavoidable during storage or even after being injected into the organism. Further, published Japanese translations of PCT international publication for patent application No. 9-505821 described that even if a 100% inclusion is achieved immediately after the liposome dispersion is prepared and separated, the included ingredients decrease in a short time via unstabilization effects due to osmotic pressure.

The radiographic contrast medium of the invention is non-orally given to a person through intravascular dosage, preferably through intravenous dosage, as injection or dripping, followed by exposure to X-rays for imaging. In CT examination, specifically for the purpose of imaging vascular lesions or tumor lesion, in general, a contrast medium of a relatively high concentration is often given in a large amount over a short time. To enable such bolus injection, requirements of the contrast medium used for imaging are flowability and low viscosity of the composition. To lower injection resistance to reduce pain of the examinee and also to avoid crisis of diapedesis, the viscosity of the solution of the composition of the invention is preferably not more than 20 mPa·s at 37° C. (when measured in the Ostwald method), more preferably not more than 18 mPa·s, and still more preferably not more than 15 mPa·s. It is occasionally desirable to be viscous to a certain extent to allow dilution with humors to slowly proceed, depending on the position of the body being imaged.

A relatively high osmole concentration imposes a burden on the heart and a circulatory system. A solution or suspension which is isotonic to blood is prepared by allowing a contrast medium material to be dissolved or suspended in a medium at a concentration giving an isotonic solution. For example, in case when an isotonic solution cannot be prepared with a contrast medium compound alone, due to its low solubility, a nontoxic water-soluble material, such as salts such as sodium chloride or saccharides, e.g., mannitol, glucose, saccharose and sorbitol may be added to form an isotonic solution or suspension.

The optimum concentration of an iodine compound is usually designed for every symptom and every kind of X-ray imaging examination. There has been revealed the amount of an iodine compound conveyed to a targeted organ to provide prescribed contrast performance in radiography, for example, as described in Japanese Patent No. 2619037. This amount basically corresponds to iodine type contrast mediums used in conventional X-ray imaging examination. The total amount of iodine inside the liposome or the total amount of iodine inside and outside the liposome may be an extent equivalent to a conventional dose. Imaging effects of parenchyma organ are mainly controlled by the dosed iodine amount per body weight unit, i.e., (concentration of contrast medium)×(dose of contrast medium) and often increase in proportion to the dosed iodine amount. For example, to achieve sufficient imaging effects of liver parenchyma, it is an amount of 600 mg I per kg of body weight. However, unfavorable occasion such as aggregation of liposome vesicles or increased viscosity must be taken into consideration at excessively high solution concentrations. The iodine content of the contrast medium prepared according to the method of the invention is usually from 30 to 500 mg I/ml at a usually assumed dose of solution of 10 to 300 ml, preferably from 150 to 500 mg I/ml, and more preferably from 250 to 400 mg I/ml.

Preferably, the radiographic contrast medium of the invention contains an iodine compound in a water phase included inside the liposome membrane and also in a water phase outside the membrane (i.e., in the aqueous medium in which liposome vesicles are dispersed, and more preferably, the respective concentrations of the iodine compound are substantially the same between inside and outside of the liposome membrane. An identical iodine compound being concurrently present inside and outside of the liposome membrane means that the iodine compound exists in different forms in the identical contrast medium. The iodine compound existing in an aqueous medium in which the liposome is dispersed moves within the body in a behavior similar to conventional iodine compound in a free form. On the other hand, the iodine compound included within the liposome is conveyed along with movement of the liposome within the body. Such a state of the contrast medium material can exhibit the following advantages in diagnostic examination. According to the use of the radiographic contrast medium of this invention, the difference in diffusion time in the body between non-capsulated contrast medium material and one which is encapsulated in the liposome gives images differing in distributive behavior with the elapse of time, which provides useful diagnostic information. A normal cell is different from a cancer cell in the developmental degree of a vascular system, properties of veins and a lymphatic vessel, which is reflected in the behavior of contrast medium material through hemodynamics and the perfusion state. The contrast medium composition of the invention can collect a lot of clinical data even when dosed only one time.

The present invention will be further described based on specific examples. Apparatuses employed in the examples, and materials shown therein and their numerical parameters such as concentration, quantity, treatment time, treatment temperature and the like, and treatment methods are only preferred examples falling within the scope of the invention.

EXAMPLE 1

Determination of Iodine of Iodine Compound

A sample (liposome dispersion) was dialyzed with an isotonic saline solution and after completion of dialysis, ethanol was added thereto to destroy the liposome and the quantity of the iodine compound included in the liposome was determined by absorptiometry. The ratio of the foregoing quantity to the total amount of the iodine compound of the sample was represented as an enclosure ratio (wt %).

Preparation of Contrast Medium

A mixture of 86 mg of dipalmitoylphosphatidylcholine (DPPC), 38.4 mg of cholesterol and 19.2 mg of PEG-phospholipid (SUNBRIGHT DSPE-020CN, lipid modified with polyethylene glycol, product by NIPPON OIL &FATS CO., LTD.) were added into a stainless steel autoclave and heated with maintaining the autoclave at 60° C., then, 13 g of liquid carbon dioxide was added thereto. While stirring, the pressure within the autoclave was increased from 50 kg/cm$^2$ to 120 kg/cm$^2$ by decreasing the internal volume of the autoclave to make carbon dioxide in the supercritical state to allow lipids to be dispersed and dissolved in supercritical carbon dioxide. Further thereto, 5 ml of a contrast medium solution which contained an iopamidol solution of 306.2 mg/ml (at an iodine content of 150 mg/ml), trometamol of 1 mg/ml and edetate calcium disodium (EDTA Na$_2$—Ca) of 0.1 mg/ml and the pH of which was adjusted to approximately 7 with hydrochloric acid or sodium hydroxide, was continuously added over a period of 50 min. using a metering pump. After completion of the addition, the inside of the autoclave was evacuated to discharge the carbon dioxide, whereby a dispersion of liposomes enclosing a contrast medium solution was obtained. The obtained dispersion was heated to 60° C. and subjected to pressure filtration using 1.0 μm and 0.45 μm cellulose type filters, produced by Advantech Co. The thus obtained liposome-containing contrast medium was designated as Sample 1-1.

Samples 1-2 to 1-5 were prepared similarly to the foregoing Sample 1-1, provided that together with DPPC and cholesterol, ethanol or PEG-phospholipid was added in the amounts shown in Table 1.

Samples 1-1 to 1-5 were measured with respect to the enclosure ratio. The enclosure ratio is a ratio of iopamidol included in the interior of the liposome to the total amount of iodine compounds, each of which is represented by equivalent converted to iodine atom.

TABLE 1

| Sample No. | PEG-phospholipid (mg) | Ethanol (mg) | Enclosure Ratio (wt %) | Ratio to CO$_2$ (wt %)* |
|---|---|---|---|---|
| 1-1 | 19.2 | 0 | 19 | 0.15 |
| 1-2 | 9.6 | 0 | 10 | 0.08 |
| 1-3 | 0 | 0 | 4 | 0 |
| 1-4 | 0 | 2000 | 7 | 0 |
| 1-5 | 0 | 8000 | 9 | 0 |

*Ratio of PEG-phospholipid to CO$_2$ (wt %)

EXAMPLE 2

Samples 2-1 to 2-8 were prepared similarly to Sample 1-1 of Example 1, provided that the contrast medium solution was varied with respect to amount or kind, as shown in Table 2.

The thus prepared samples were measured with respect to the iodine content, using a spectrophotometer to determine the enclosure ratio.

TABLE 2

| Sample No. | Contrast Medium Solution | Iodine Content (mg/ml) | Enclosure Ratio (wt %) |
|---|---|---|---|
| 2-1 | Iopamidol solution | 150 | 19 |
| 2-2 | Iopamidol solution | 250 | 18 |
| 2-3 | Iopamidol solution | 300 | 15 |
| 2-4 | Iopromide solution | 240 | 16 |
| 2-5 | Iohexol solution | 180 | 18 |
| 2-6 | Iohexol solution | 300 | 14 |
| 2-7 | Iomeprol solution | 300 | 13 |
| 2-8 | Ioxilan solution | 300 | 14 |

EXAMPLE 3

Determination of Liposome Vesicle Size

Liposome vesicle size was determined in the following manner. A dispersion containing liposome vesicles enclosing an iodine compound was frozen and fractured, following which carbon was vapor-deposited onto the fractured interfaces and the deposited carbon was observed by an electron microscope (freeze fracture TEM method). The particle size was defined as an arithmetic average of the sizes of 20 liposome particles observed.

Preparation of Contrast Medium

A mixture of 192 mg of dipalmitoylphosphatidylcholine (DPPC), 76.8 mg of cholesterol and 38.4 mg of PEG-phospholipid (SUNBRIGHT DSPE-020CN, phospholipid modified with polyethylene glycol, product by NIPPON OIL & FATS CO., LTD.) were added into a stainless steel autoclave and heated with maintaining the autoclave at 60° C., then, 13 g of liquid carbon dioxide was added thereto. While stirring, the pressure within the autoclave was increased to 120 kg/cm$^2$ from 50 kg/cm$^2$ by decreasing the internal volume of the autoclave to bring the carbon dioxide to the supercritical state, which allowed lipids to be dispersed and dissolved in supercritical carbon dioxide. Further thereto, 10 ml of a contrast medium solution which contained an iopamidol solution of 306.2 mg/ml (at an iodine content of 200 mg/ml), trometamol of 1 mg/ml and edetate calcium disodium (EDTA Na$_2$—Ca) of 0.1 mg/ml, and the pH of which was adjusted to approximately 7 with hydrochloric acid or sodium hydroxide, was continuously added over a period of 50 min. using a metering pump. After completing the addition, the inside of the autoclave was evacuated to discharge carbon dioxide, whereby a dispersion of liposomes enclosing a contrast medium solution was obtained. The obtained dispersion was heated to 60° C. and subjected to pressure filtration using a 1.0 μm cellulose type filter, produced by Advantech Co. The thus obtained liposome-containing contrast medium was designated as Sample 3-1.

Samples 3-2 to 3-4 were prepared similarly to Sample 3-1, provided that the contrast medium concentration (iodine content) was varied as shown in Table 3. The amount of iodine enclosed in the interior of the liposome (also denoted simply as enclosed iodine amount) and the enclosure ratio were determined in the method described earlier. The liposome vesicle size was determined in the above method.

TABLE 3

| Sample No. | Contrast Medium Concentration (mg/ml) | Total Lipid Amount (mg/ml) | Liposome Particle Size (μm) | Enclosure Ratio (%) | Enclosed Iodine Amount (mg/ml) | Pressure Filtration Rate (g/min) | Aging Dispersion Stability 1 month | Aging Dispersion Stability 3 months |
|---|---|---|---|---|---|---|---|---|
| 3-1 | 200 | 30.7 | 0.4 | 15 | 30 | 1.0 | 4 | 3 |
| 3-2 | 240 | 30.7 | 0.4 | 15 | 36 | 1.0 | 5 | 5 |
| 3-3 | 250 | 30.7 | 0.4 | 15 | 37.5 | 1.0 | 5 | 5 |
| 3-4 | 300 | 30.7 | 0.42 | 12 | 36 | 0.5 | 4 | 4 |

Measurement of Pressure Filtration Rate

Using a 1.0 μm cellulose filter (2 cm diameter) used in the preparation of the foregoing contrast mediums, the pressure filtration time was measured, which was divided by the amount of passed liquid to determine the pressure filtration rate. A rate of not more than 0.2 ml/min is not acceptable in terms of industrial manufacturing efficiency.

Aging Stability of Dispersion

The obtained liposome contrast mediums were each put into a 20 ml vial and capped and the periphery of the cap was shielded with a seal tape. The thus prepared samples were allowed to stand in a dark place under an environment of 23° C. and 55% RH for 1 month and 3 months. Thus aged samples were visually evaluated based on the following criteria:

5: no deposit was observed, nor changed since preparation,
4: slight turbidity was observed but no separation nor deposition was noted,
3: higher turbidity was observed but no separation nor deposition was not noted,
2: deposits were produced,
1: transparent liquid and white deposits were completely separated.

EXAMPLE 4

Preparation of Contrast Medium

A mixture of 368.4 mg of dipalmitoylphosphatidylcholine (DPPC), 147.4 mg of cholesterol and 111.5 mg of PEG-phospholipid (SUNBRIGHT DSPE-020CN, phospholipid modified with polyethylene glycol, product by NIPPON OIL & FATS CO., LTD.) were added into a stainless steel autoclave and heated with maintaining the autoclave at 60° C., then, 13 g of liquid carbon dioxide was added thereto. While stirring, the pressure within the autoclave was increased to 120 kg/cm$^2$ from 50 kg/cm$^2$ by decreasing the internal volume of the autoclave to bring the carbon dioxide to the supercritical state which allowed lipids to be dispersed and dissolved in supercritical carbon dioxide. Further thereto, 13 ml of a contrast medium solution which contained an iopamidol solution of 306.2 mg/ml (at an iodine content of 150 mg/ml), tromethamol of 1 mg/ml and edetate calcium disodium (EDTA Na$_2$—Ca) of 0.1 mg/ml and the pH of which was adjusted to approximately 7 with hydrochloric acid or sodium hydroxide, was continuously added over a period of 50 min. using a metering pump. After completion of the addition, the inside of the autoclave was evacuated to discharge carbon dioxide, whereby a dispersion of liposomes including a contrast medium solution was obtained. The obtained dispersion was heated to 60° C. and subjected to pressure filtration using a 0.45 μm cellulose type filter, produced by Advantech Co. The thus obtained liposome-containing contrast medium was designated as Sample 4-1.

Samples 4-2 to 4-8 were prepared similarly to Sample 4-1, provided that lipid composition, the contrast medium concentration or the total lipid amount was varied as shown in Table 4.

Sample 4-9 was prepared in the following manner. A mixture of 368.4 mg of dipalmitoylphosphatidylcholine (DPPC), 147.4 mg of cholesterol and 111.5 mg of PEG-phospholipid (SUNBRIGHT DSPE-020CN, phospholipid modified with polyethylene glycol, product by NIPPON OIL & FATS CO., LTD.) was mixed with 10 ml of a mixture of chloroform, ethanol and water (by weight ratio of 100:20:0.1) in a messflask. The prepared mixture was heated on a water bath (65° C.) and evaporated using a rotary evaporator to allow solvents to be distilled away. The residue was dried in vacuo for 2 hr. to form lipid film. Further thereto, 13 ml of the foregoing contrast medium solution was added and the obtained mixture was stirred by a mixer for about 10 min., while heating at 65° C. A dispersion of liposome containing a contrast medium solution was obtained by further stirring. The obtained dispersion was heated to 60° C. and subjected to pressure filtration using 1.0 μm and 0.45 μm cellulose type filters, produced by Advantech Co. to obtain a liposome-containing contrast medium.

TABLE 4

| Sample No. | DPPC | Cholesterol (molar ratio*) | DSPE-020CN (molar ratio*) | Contrast Medium Concentration (mg/ml) | Total Lipid Amount (mg/ml) | Particle Size (μm) | Enclosure Ratio (%) | Filtration Rate** (g/min) |
|---|---|---|---|---|---|---|---|---|
| 4-1 | 100 | 76 | 6 | 150 | 23.6 | 0.40 | 17 | 2.0 |
| 4-2 | 100 | 76 | 9 | 250 | 48.2 | 0.40 | 18 | 1.2 |
| 4-3 | 100 | 76 | 6 | 150 | 18.0 | 0.40 | 13 | 2.1 |
| 4-4 | 100 | 76 | 6 | 150 | 90.0 | 0.42 | 14 | 0.8 |
| 4-5 | 100 | 80 | 15 | 250 | 48.2 | 0.38 | 13 | 1.0 |
| 4-6 | 100 | 65 | 15 | 250 | 48.2 | 0.39 | 14 | 1.2 |
| 4-7 | 100 | 100 | 9 | 250 | 48.2 | 0.40 | 14 | 0.5 |

TABLE 4-continued

| Sample No. | DPPC | Cholesterol (molar ratio*) | DSPE-020CN (molar ratio*) | Contrast Medium Concentration (mg/ml) | Total Lipid Amount (mg/ml) | Particle Size (μm) | Enclosure Ratio (%) | Filtration Rate** (g/min) |
|---|---|---|---|---|---|---|---|---|
| 4-8 | 100 | 50 | 6 | 150 | 23.6 | 0.39 | 13 | 1.5 |
| 4-9 | 100 | 76 | 6 | 150 | 23.6 | 0.40 | 5 | 0.3 |

*molar ratio, based on DPPC
**pressure filtration using 0.45 μm filter

Liposome Vesicle Size

The average vesicle size of the respective contrast medium samples was determined according to the method described earlier.

Evaluation of Enclosure Ratio

The obtained liposome contrast medium samples were each put into a 20 ml vial and capped with a cap, and the periphery of the cap was shielded with a seal tape. The thus prepared samples were allowed to stand in a dark place under an environment of 23° C. and 55% RH for 2 month. Thereafter, samples were each dialyzed with an isotonic saline solution and after completion of dialysis, ethanol was added thereto to destroy the liposome to determine the amount of the iodine compound included within the liposome through absorptiometry. The ratio of the amount of included iodine compound to the total amount of iodine compound was represented as an enclosure ratio (%). After aged for 2 months, incomplete or unstable liposome particles released contents through rupture, coagulation or leakage, resulting in lowering of the enclosure ratio.

Measurement of Pressure Filtration Rate

Using a 0.45 μm cellulose filter (2 cm diameter) used in the preparation of the foregoing contrast mediums, the pressure filtration rate was eveluated similarly to Example 3.

As can be seen from Table 4, contrast mediums exhibiting an enhanced enclosure ratio and superior pressure filterability were prepared according to the invention.

What is claimed is:

1. A method of preparing a radiographic contrast medium comprising a liposome, the method comprising the steps of:
   (a) combining at least one phospholipid selected from the group consisting of phosphatidylcholine, phosphatidylserine, phosphatidylinositol, phosphatidylglycerol, phosphatidylethanolamine, sphingomyelin, phosphatidic acid, dipalmitoylphosphatidylcholine, distearoylphosphatidylcholine, dimyristoylphosphatidylcholine, dioleylphosphatidylcholine, dipalmitoylphosphatidylglycerol, distearoylphosphatidylserine, distearoylphosphatidylglycerol, dipalmotoylphosphatidylinositol, distearoylphosphatidylinositol, dipalmitoylphosphatidic acid, distearoylphosphatidic acid, 1,2-dioleoyloxy-3-(trimethylammonium)propane, N,N-dioctadecylamidoglycylspermine, dimethyloctadecylammonium bromide, N-[1-(2,3-dioleyloxy)propyl]-N,N,N-trimethylammonium chloride, 2,3-dioleyloxy-N-[2(spermine-carboxamido)ethyl]-N,N-dimethyl-1-propaneaminiumtrifluoroacetate and N-[1-(2,3-dimyristyloxy)propyl]-N,N-dimethyl-N-(2-hydroxyethyl)ammonium bromide, a sterol and a lipid containing a polyalkyleneoxide group with liquid carbon dioxide in a pressure vessel and then increasing a pressure within the pressure vessel to form a super critical carbon dioxide,
   (b) adding thereto an aqueous solution containing at least one iodine compound selected from the group consisting of iomeprol, iopamidol, iohexol, iopentol, iopromide, ioxilane, iosimide, iobenzol, iotrolan, iodixanol, iodecimol, iotasl, metrizamide, 1,3-bis-[N-3,5-bis-(2,3-dihydroxypropylaminocarbonyl)-2,4,6-triiodophenyl]-N-hydroxyacetyl-amio]-propane, diatrizoic acid, sodium diatrizoate, meglumine diatrizoate, acetorizoic acid, diprotrizo acid, iodamide, sodium iodipamide, meglumine iodipamide, iodohippuric acid, iodomethamic acid, iodopyracet, iodo-2-pyrridone-N-acetic acid, 3,5-diiodo-4-pyridone-N-acetic acid, iothalamic acid, metrizoic acid, iopanoic acid, iocetamic acid, iophenoic acid, sodium thyropanoate and sodium iopodate to form micelles and
   (c) discharging the carbon dioxide to form liposomal vesicles enclosing the iodine compound.

2. The method of claim 1, wherein the lipid containing a polyalkyleneoxide group is a lipid containing a polyethyleneoxide group.

3. The method of claim 1, wherein the lipid containing a polyalkyleneoxide group is contained in an amount of 0.01 to 1% by weight of the carbon dioxide.

4. The method of claim 1, wherein the liposomal vesicles are unilamellar or several-lamellar vesicles.

5. The method of claim 1, wherein the iodine compound is contained in an iodine atom amount of 100 to 350 mg I per ml of contrast medium.

6. The method of claim 1, wherein the iodine compound is selected from the group consisting of iomeprol, iopamidol, iohexol, iopentol, iopromide, ioxilane, iosimide, iobenzol, iotrolan, iodixanol, iodecimol, iotasl, metrizamide, and 1,3-bis-[N-3,5-bis-(2,3-dihydroxypropylaminocarbonyl)-2,4,6-triiodophenyl]-N-hydroxyacetyl-amio]-propane.

7. The method of claim 6, wherein the iodine compound is selected from the group consisting of iomeprol, iopamidol, iohexol, iopromide, ioxilane, iotasl, iotrolan and iodixanol.

8. The method of claim 1, wherein the liposomal vesicles are dispersed in an aqueous medium, and 70% to 95% by weight of the iodine compound is not enclosed in the liposome vesicles but exists in the aqueous medium.

9. The method of claim 1, wherein whole lipids contained in the contrast medium is 20 to 100 mg/ml.

10. The method of claim 9, wherein a weight ratio of the iodine compound enclosed in the liposomal vesicles to the whole lipids is 3 to 8.

11. The method of claim 5, wherein the iodine compound is contained in an iodine atom amount of 200 to 300 mg I per ml of contrast medium and whole lipids contained in the contrast medium is 20 to 80 mg/ml.

12. The method of claim 11, wherein the iodine compound is contained in an iodine atom amount of 240 to 300 mg I per ml of contrast medium.

13. The method of claim 1, wherein a molar ratio of the phospholipid to the sterol is from 100/60 to 100/90.

14. The method of claim 1, wherein a molar ratio of the phospholipid to the lipid containing a polyalkyleneoxide group is from 100/5 to 100/10.

15. The method of claim 1, wherein the liposome vesicles exhibit an average size of 0.05 to 0.8 μm.

16. The method of claim 1, wherein the aqueous solution further comprises at least one compound selected from the group consisting of a water-soluble amine buffer, edetate calcium disodium, an inorganic salt, an osmotic pressure-adjusting agent and a preservative.

17. The method of claim 1, wherein each of aqueous phases inside and outside the liposome vesicles contains cations as chloride salts, phosphate salts or hydrogen carbonate salts and satisfies the following requirement:

$$[Na^+]+126.[Ca^{2+}]+50.[K^+] \leq 130$$

wherein $[Na^+]$ is a sodium ion content of 20 to 70 mM, $[Ca^+]$ is a calcium ion content of 0.1 to 0.6 mM and $[K^+]$ is a potassium ion content of 0.4 to 0.8 mM; and a magnesium ion content is 0.5 to 0.8 mM.

* * * * *